US008822515B2

(12) United States Patent
Smith et al.

(10) Patent No.: US 8,822,515 B2
(45) Date of Patent: Sep. 2, 2014

(54) HETEROCYCLIC BENZOXAZOLE COMPOSITIONS AS INHIBITORS OF HEPATITIS C VIRUS

(75) Inventors: Paul Smith, Baltimore, MD (US); Dawn Ward, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 270 days.

(21) Appl. No.: 13/502,244

(22) PCT Filed: Oct. 18, 2010

(86) PCT No.: PCT/US2010/053085
§ 371 (c)(1),
(2), (4) Date: Apr. 16, 2012

(87) PCT Pub. No.: WO2011/047390
PCT Pub. Date: Apr. 21, 2011

(65) Prior Publication Data
US 2012/0208856 A1    Aug. 16, 2012

Related U.S. Application Data

(60) Provisional application No. 61/252,235, filed on Oct. 16, 2009.

(51) Int. Cl.
*A61K 31/42* (2006.01)
*C07D 263/57* (2006.01)
*C07D 413/04* (2006.01)

(52) U.S. Cl.
CPC .............. *C07D 413/04* (2013.01); *A61K 31/42* (2013.01); *C07D 263/57* (2013.01)
USPC .......................................... 514/374; 548/224

(58) Field of Classification Search
CPC .............................. A61K 31/42; C07D 263/57
USPC .......................................... 514/374; 548/224
See application file for complete search history.

(56) References Cited

U.S. PATENT DOCUMENTS

| | | | |
|---|---|---|---|
| 6,288,091 | B1 | 9/2001 | Crute et al. |
| 6,348,477 | B1 | 2/2002 | Crute et al. |
| 6,887,877 | B2 | 5/2005 | Chan Chun Kong et al. |
| 2006/0293320 | A1 | 12/2006 | Schmitz et al. |
| 2007/0032497 | A1 | 2/2007 | Hashimoto et al. |

FOREIGN PATENT DOCUMENTS

WO    WO 2005-121132    12/2005

OTHER PUBLICATIONS

International Search Report of corresponding PCT Application PCT/US2010/53085, (2010).
De Francesco, R. and Migliaccio, G. Challenges and successes in developing new therapies for hepatitis C; Nature 2005, 436: 953-960.
WHO; Journal of Viral Hepitis: 1999, 6: 35-47.
NIH; What I need to know about Hepatitis C; NIH Publication No. 09-4229; 2009; vol. 2009.
Frick, D. N.; The Hepatitis C. Virus NS3 Protein: A Model RNA Helicase and Potential Drug Target; Curr. Issues Molecular Biology 2007, 9: 1-20.
Sakamoto, N. and Watanabe, M.; New therapeutic approaches to hepatitis C virus; Journal of Gastroenterology 2009, 44: 643-649.
Wardell, A.D., Errington, W., Ciaramella, G., Merson, J. and McGarvey MJ.; Characterization and mutational analysis of the helicase and NTPase activities of hepatitis C virus full-length NS3 protein; J. General Virology 1999, 80: 701-709.
Gordon, C.P. and Keller, P.A.; Control of Hepatitis C: A Medicinal Chemistry Perspective; Journal of Medicinal Chemistry 2005, 48: 1-20.
Zhang, N., Chen, H-M., Koch, V., Schmitz, H., Liao, C-L., Bretner, M., Bhadti, V. S., Fattom, A. I., Naso, R. B., Hosmane, R. S., Borowski; Ring-Expanded ("Fat") Nucleoside and Nucleotide Analogues Exhibit Potent in Vitro Activity against Flaviviridae NTPases/Helicases, Including Those of the West Nile Virus, Hepatitis C Virus, and Japanese Encephalitis Virus; P.J. Med. Chem. 2003, 46: 4149-4164.
Zhang, P., Zhang, N., Buckwold, V. E., and Hosmane; Chemical and biological effects of substitution of the 2-position of ring-expanded ("fat") nucleosides containing the imidazo diazepine-4,8-dione ring system: The role of electronic and steric factors on glycosidic bond stability and anti-HCV activity; R. S. Bioorg. Med. Chem. 2007,15: 4933-4945.
Reynolds, M., DeLuca, M., and Kerwin, S. M.; The Novel Bis(benzoxazole) Cytotoxic Natural Product UK-1 is a Magnesium Ion-Dependent DNA Binding Agent and Inhibitor of Human Popoisomerase II; Bioorg. Chem. 1999, 27: 326-337.
Ueki, M., Ueno, K., Miyadoh, S., Abe, Shibata, K., Tanguchi, M., and Oi, S.; UK1, A Novel Cytotoxic Metabolite from Stroptomyces; J. Antibiotics 1993, 46: 1089-1094.
Sehested, M. A. J., P.B.; Mapping of DNA Topoisomerase II Poisons (Etoposide, Clerocidin) and Catalytic Inhibitors (Aclarubicin, ICRF-187) to Four Distinct Steps in the Topoisomerase II Catalytic Cycle; Biochem. Pharm. 1996, 51: 879-886.
Yedavalli, V. S. R. K., Zhang, N., Cai, H., Zhang, P., Starost, M. F., Hosmane, R. S., and Jeang, K-T.; Ring Expanded Nucleoside Analogues Inhibit RNA Helicase and Intracellular Human Immunodeficiency Virus Type 1 Replication; Journal of Medicinal Chemistry 2008, 51: 5043-5051.
Marchand, C., Johnson, A., Karki, R., Pais, G. C., Zhang, X., Cowansage, K., Patel, T., Nicklaus, M., Burke Jr., T., and Pommier, Y.; Metal-Dependent Inhibition of HIV-1 Integrase by Diketo Acids and Resistance of the Soluble Double-Mutant (F185K/ C280S); Mol. Pharma. 2003, 64: 600-609.
Maurin, C., Bailly, F., and Cotelle, P.; Structure-Activity Relationships of HIV-1 Integrase Inhibitors—Enzyme-Ligand Interations; Curr. Med. Chem. 2003, 10: 1795-1810.

(Continued)

Primary Examiner — Raymond Henley, III
(74) Attorney, Agent, or Firm — Todd Juneau; Wendy Martin

(57)    ABSTRACT

This invention relates to benzoxazole compounds, compositions and devices for delivering them, processes for manufacturing them, and methods of using them in the treatment of Hepatitis C Virus.

7 Claims, No Drawings

(56) References Cited

OTHER PUBLICATIONS

Grobler, J. A., Stillmock, K., Hu, B., Witmer, M., Felock, P., Espeseth, A. S., Wolfe, A., Egbertson, M., Bourgeois, M., Melamed, J., Wai, J.S., Young, S., Vacca, J., and Hazuda, D. J.; Diketo acid inhibitor mechanism and HIV-1 integrase: Implications for metal binding in the active site of phosphotransferase enzymes; *Proc. Natl. Acad. Sci. USA* 2002, 99: 6661-6666.

Kumar, D., Jacob, M. R., Reynolds, M. B., and Kerwin, S. M.; Synthesis and Evaluation of Anticancer Benzoxazoles and Benzimidazoles Related to UK-1; *Bioorg. Med. Chem. Lett.* 2002, 10: 3997-4004.

Wang, B., Maghami, N., Goodlin, V., and Smith, P. J.; Critical structural motif for the catalytic inhibition of human topoisomerase II by UK-1 and analogs; *Bioorg. Med. Chem. Lett.* 2004, 14: 3221-3226.

Cate, L. A.; An Efficient Carboxylation of 1-Naphthols using Magnesium Methyl Carbonate; *Synthesis* 1983: 385-386.

Henary, M. M., and Fahrni, C.J.; Excited-State Intramolecular Proton Transfer in 2-(2'-Tosylaminophenyl) benzimidazole; *J. Phys. Chem. A.* 2002, 106: 5210-5220.

Borowski, P., Kuehl, R., Mueller, O., Hwang, L-H., Schulze zur Wiesch, J.; Biochemical properties of a minimal functional domain with ATP-binding activity of the NTPase/helicase of hepatitis C virus; *Eur. J.Biochem.* 1999, 266: 715-723.

Borowski, P., Mueller, O., Niebhr, A., Kalitzky, M., Hwang, L-H; ATP-binding domain of NTPase/helicase as a target for hepati-tis C antiviral therapy; *Acta Biochim. Polon.* 2000, 47: 173-180.

HETEROCYCLIC BENZOXAZOLE COMPOSITIONS AS INHIBITORS OF HEPATITIS C VIRUS

CROSS REFERENCE TO RELATED APPLICATIONS

This application claims priority filing date benefit under 35 USC 119(e) to U.S. patent application 61/252,235, filed Oct. 16, 2009, the contents of which are incorporated herein in their entirety.

STATEMENT REGARDING FEDERALLY SPONSORED RESEARCH OR DEVELOPMENT

This invention was made with government support under r25-GM55036 awarded by NIGMS, and P217A030141 awarded by U.S. Dept. of Education. The government has certain rights in the invention.

BACKGROUND

1. Field of the Invention

This invention relates to small molecule benzoxazole compounds useful as inhibitors of Hepatitis C Virus.

2. Background of the Invention

Hepatitis C Virus (HCV) affects approximately 170 million people worldwide. The blood-born illness has clinical symptoms that are generally benign or subacute, leaving patients without knowledge of the disease until it is manifested as chronic liver damage 1-3 decades later. Infection can lead to liver damage, cirrhosis of the liver, liver cancer, and liver failure.

An enveloped virus belonging to the Flaviviridae family, HCV has a positive strand RNA genome of approximately 10 kilobases that encodes a polyprotein of approximately 3000 amino acids. The N-terminus of the polyprotein is cleaved into three structural proteins (core, E1, E2) and the C-terminus is cleaved into seven mature nonstructural (NS) proteins (p7, NS2, NS3, NS4A, NS4B, NS5A, NS5B). The NS3 protein is a promising target for intervention due to its enzymatic activities, acting as a serine protease, an RNA-stimulated nucleoside triphosphatase (NTPase) and an RNA helicase. HCV helicase activity is essential for viral replication and requires $Mg^{2+}$ and ATP. In the genomic process, Flaviviridae viruses synthesize negative-stranded RNA using the parentally positive-stranded RNA as a template. The resulting negative-stranded RNA is used as the template to synthesize a positive-stranded progeny RNAs that are assembled into viral particles.

Therapies for HCV have primarily focused on reverse transcriptase and protease, two of the three virally-encoded enzymes. These are not effective in all patients, with the virus remaining active in some host tissues. The current treatment of peginterferon and ribavirin achieves only a 40-50% sustained viral response (SVR) rate. Moreover, the vast majority of the patient have to prematurely halt treatment due to complications arising from undesirable side effects. Therefore, new treatments are needed that are more effectual and better tolerated.

BRIEF SUMMARY OF THE INVENTION

In a preferred embodiment of the present inventive subject matter, there is provided a compound, which comprises:

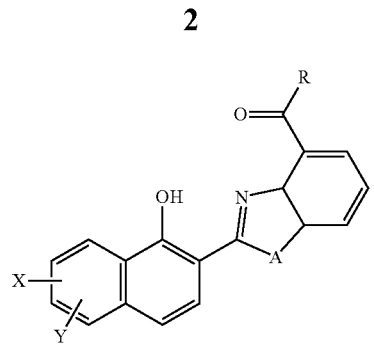

wherein
A is N, S, or O;
R is independently a hydrogen, amino, alkylamino, dialkylamino, hydroxy, or alkoxy radical; and,
X and Y are independently a hydrogen, amino, alkylamino, dialkylamino, alkylacylamino, hydroxy, alkoxy, alkyl, alkenyl, or arylacylamino radical optionally substituted by 1-3 radicals of alkyl, alkenyl, amino, alkylamino, hydroxy, alkoxy, aryl or heteroaryl.

In one preferred aspect, there is provided a compound as described herein or a pharmaceutically acceptable salt thereof, wherein
R is independently a hydrogen hydroxy, aminoalkyl, or alkoxy radical; and,
X and Y are independently a hydrogen, alkyl, aryl, alkoxy, aryloxy, alkylamino, arylamino, alkylacylamino or arylacylamino radical.

In another preferred aspect, there is provided a compound as described herein or a pharmaceutically acceptable salt thereof, wherein
A is O;
R is independently a hydroxy, aminoalkyl, or alkoxy radical;
X is a benzyloxy radical; and
Y is a hydrogen radical.

In another preferred embodiment, there is provided a pharmaceutical composition comprising a compound as described herein and a pharmaceutically acceptable carrier.

In another preferred embodiment, there is provided a method of prophylaxis or treatment of Hepatitis C Virus infection in a mammal, comprising administering an effective amount of the compound as described herein.

In another preferred embodiment, there is provided a method of prophylaxis or treatment of Hepatitis C Virus infection in a mammal, comprising administering an effective amount of the pharmaceutical composition described herein.

In another preferred embodiment, there is provided a method of prophylaxis or treatment of Hepatitis C Virus infection in a mammal, comprising administering an effective amount of the compound selected from the group consisting of compound 1, 8, 9, and 10.

DETAILED DESCRIPTION OF THE INVENTION

One target of current intense interest is the virally-encoded RNA helicase from HCV. Accordingly, the compounds were tested against HCV NTPase/helicase and were found to be active. To determine if this enzyme inhibition produces viral inhibition in a cellular setting, these were further screened using a replicon assay and found to exhibit similar potency. The design and synthesis of the novel HCV inhibiting compounds are provided herein.

Results and Discussion

Target compounds 2a and 2b are provided below.

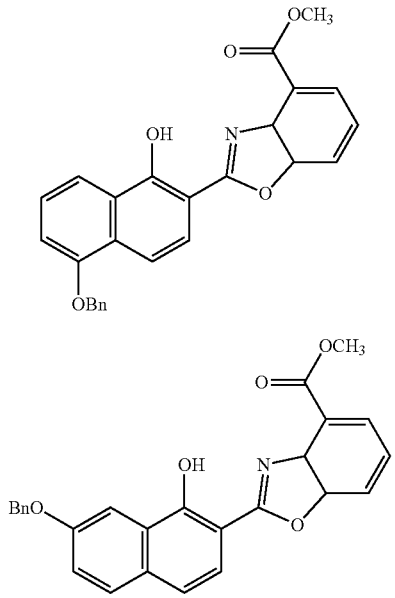

Compound Structures No. 2a and b

Synthesis.

The dihydroxynapthoic acids required as starting materials for 2a or 2b were prepared by reaction of corresponding diol 3a or 3b with magnesium methyl carbonate as previously described (Scheme 1).[19] The dihydroxynaphthoic acids were then protected using benzyl chloride, yielding tribenzyl derivatives that upon hydrolysis gave dibenzyloxynapthoic acid 4a or 4b. Amide formation between these and methyl 3-hydroxyanthranilate was accomplished using N,N-carbonyldiimidazole (CDI), and subsequent heating of the amide products with pyridinium p-toluenesulfonate (PPTS) in anhydrous m-xylene resulted in cyclodehydration, providing the corresponding benzoxazole 5a or 5b.

Scheme 1: Synthesis of the Naphthyl Benzoxazole Compounds

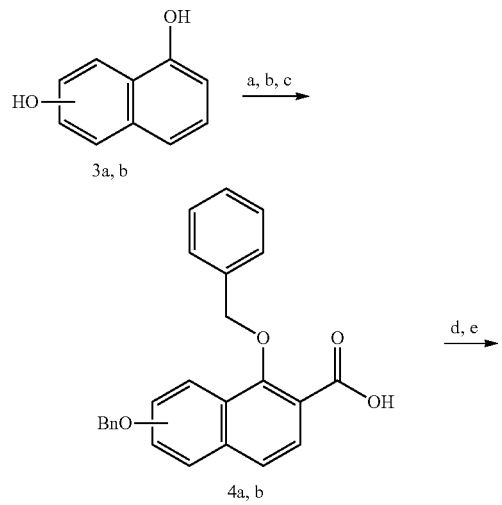

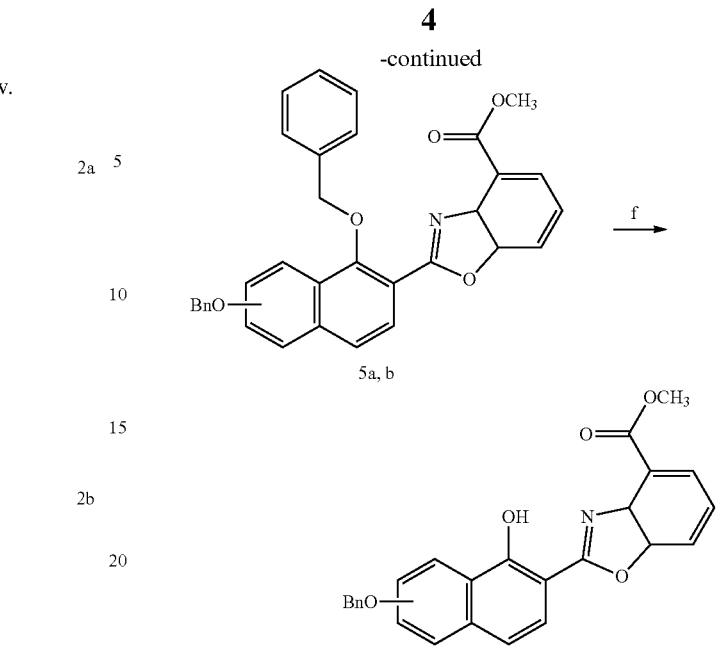

Reagent conditions a. DMF, methyl magnesium carbonate, 140° C., 5 h, ice, HCl b. BnCl, DMF, K₂CO₃, 140° C. c. aq. NaOH, MeOH, citric acid d. CDI, THF, 25° C., 15 mins, then added methyl-3-hydroxyanthranilate, reflux 20-25 h. e. PPTS, m-xylene, 140° C., 5 h. f. H₂, 10% Pd/C, EtOAc.

The final step required selective deprotection of the 1'-hydroxyl group (in preference to the 5' or 7' hydroxyl group). We found that extending the cyclodehydration reaction time (e, Scheme 1) led to removal of a single benzyl group from 5a or 5b. Moreover, reaction of 5a or 5b with hydrogen over palladium on carbon resulted in the removal of the same single benzyl group. It was not initially clear, however, that the desired benzyl group (at the 1'-position) was the one that had been removed; the possible isomeric products were not distinguishable by standard spectroscopic characterization and the results from difference NOE and NOESY experiments proved inconclusive. Ultimately, fluorescence experiments were used to confirm the product structures based on the large Stokes shift associated with the 2-(2'-hydroxylphenyl)benzoxazole substructure. As indicated in Scheme 2, compounds of this type undergo excited state intramolecular proton transfer (ESIPT), giving rise to large Stokes Shifts in their emission spectra.[20] 2-(1'-Hydroxynaphthyl)benzoxazoles 2a and 2b would also undergo ESIPT as they contain a free hydroxyl group ortho to the 2-position of the benzoxazole moiety. To determine that the correct benzyl group was removed in each case, thus validating the structures of the final products, two additional compounds were synthesized. Compound 6 (Compound Structure(s) No. 3) contains a single hydroxyl group correctly situated for ESIPT and serves as a positive control; and compound 7 contains no hydroxyl group, rendering it incapable of ESIPT, serves as a negative control.

Scheme 2: 2-(2'-hydroxyphenyl) benzoxazoles undergoes ESIPT

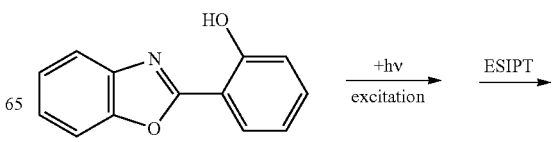

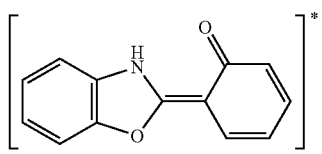

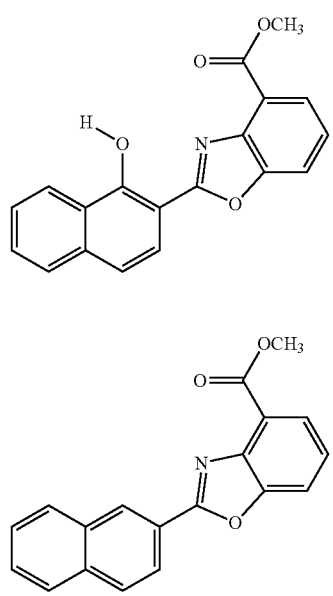

Compound Structure(s) No. 3:

Synthetic compounds used to validate that the correct benzyl was removed from target compounds 6 is the positive control and 7 is the negative control.

The results of the experiment demonstrate that the compounds 2a (Δλmax=145 nm) and 2b (Δλmax=145 nm) as well as the positive control 6 (Δλmax=137 nm) undergo ESIPT, exhibiting large Stokes Shifts. The negative control 7 (Δλmax=43 nm) exhibits a much smaller Stokes shift in comparison to 2a, 2b, and 6; which all contain ortho hydroxyl groups. These results are similar to those obtained by Henary and co-workers; consequently, we were able to conclude that selective deprotection yielded the correct products.

Compounds 2a, 2b and 6 were tested against integrase and found to be inactive. The flaviviridae family of viruses was chosen for investigation.

NTPase/Helicase Activity.

The compounds were analyzed for activity against several NTPase/helicases of the flavivirdae family including HCV, Japanese Encephalitus Virus (JEV) and Dengue Virus (DENV) and proved to be selective for HCV. Inhibitory activity of HCV was measured using a DNA substrate. The DNA substrate data show that compounds 1, 2a, 2b, and 6 inhibit the NTPase/helicase of HCV (Table 1). Furthermore, compounds 2a, 2b, and 6 still proved to be inhibitory when analyzed against the RNA substrate, but 1 was not. However, the activity is slightly decreased in the presence of the RNA substrate. A separate analysis with ATPase shows no inhibition with any of the compounds.

TABLE 1

NTPase/Helicase Assay Data: $IC_{50}$ values in μg/mL

| Compound | HCV Helicase ($IC_{50}$) | | ATPase ($IC_{50}$) |
|---|---|---|---|
| | DNA | RNA | |
| 2a | 1.6 (3.8 μM) | 8.7 (20 μM) | >500 |
| 2b | 1.1 (2.6 μM) | 8.4 (20 μM) | >500 |
| 6 | 172 (539 μM) | 189 (591 μM) | >500 |

Activity Against Hepatitis C Virus.

To determine if the compounds are active in whole cells, they were screened using an HCV replicon assay. The assay data showed that the inventive compounds were active against HCV; additionally this data indicates that compounds 2a and 2b are more active in the whole cell assays (Table 2). The latter compounds, with the benzyloxy groups at the 5- or 7-position, are less active than rIFNa-2b, but are more than ten times less cytotoxic (Table 2). Compound 2b also has similar selectivity towards HCV as human interferon alpha-2b (rIFNa-2b), the positive control. Compound 6, which lacks the 1'-benzyl and a benzyloxy group, is more cytotoxic and less selective towards HCV than the positive control.

TABLE 2

Replicon Assay Data for Target Compounds

| Compound | Virus | High Test Conc | Drug Units | $EC_{50}$ (μM) | $IC_{50}$ (μM) | $SI_{50}$ (μM) |
|---|---|---|---|---|---|---|
| rIFNa-2b | HCV | 2 | μM | 0.07 | >2 | >28.6 |
| 2a | HCV | 20 | μM | 1.13 | >20 | >17.7 |
| 2b | HCV | 20 | μM | 0.47 | >20 | >42.6 |
| 6 | HCV | 20 | μM | 0.21 | 1.61 | 7.67 |
| rIFNa-2b | HCV | 2 | μM | 0.04 | >2 | >50 |

Once the compounds proved active in the luciferase based replicon assay, they were analyzed in the RNA based confirmatory assay. The data shows slightly less inhibitory activity than in the presence of the DNA substrate, however the inhibitory activity is still comparable and the cytotoxicity is far less than that of the control rIFNa-2b (Table 3).

TABLE 3

RNA Based Confirmatory Assay Data

| Compound | Virus | High Test Conc | Drug Units | $EC_{50}$ (μM) | $IC_{50}$ (μM) | $SI_{50}$ (μM) |
|---|---|---|---|---|---|---|
| 2a | HCV | 20 | μM | | | |
| 2b | HCV | 20 | μM | | | |
| 6 | HCV | 20 | μM | 1.32 | 1.68 | >1.27 |
| rIFNa-2b | HCV | 2 | μM | 0.24 | >2 | >8.34 |

Synthesis and Testing of Previously Known Compounds
Synthesis.

UK-1 was synthesized as previously reported in (18) Wang, B., Maghami, N., Goodlin, V., and Smith, P. J. *Bioorg. Med. Chem. Lett.* 2004, 14, 3221-3226; and (19) Cate, L. A. *Synthesis* 1983, 385-386.

Four additional compounds tested included UK-1 (1), a truncated analog of UK-1 (8, Compound Structure(s) No. 4), a truncated analog of UK-1 lacking the methyl ester (9), termed the minimal acid by our group and a truncated analog of UK-1 with an amide functional group (10).

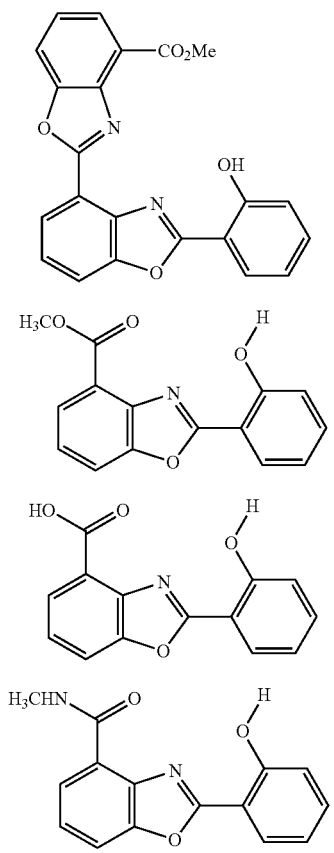

Compound Structure(s):
UK-1 (1), minimal analog (8), minimal acid (9), and minimal amide (10)

Despite that the novel compounds were inactive against integrase, UK-1 and analogs were tested.

TABLE 4

NTPase/Helicase Assay Data: $IC_{50}$ values in µg/mL

| Compound | HCV Helicase ($IC_{50}$) | | ATPase ($IC_{50}$) |
|---|---|---|---|
| | DNA | RNA | |
| 1 | 146 | >500 | >500 |
| 8 | >500 | >500 | >500 |
| 9 | >500 | >500 | >500 |
| 10 | >500 | >500 | >500 |

Activity Against Hepatitis C Virus. To determine if the compounds are active in whole cells, they were screened using an HCV replicon assay. The assay data showed compounds 1, 8, 9, and 10, which previously tested inactive against HCV NTPase/helicase, were active against HCV.

TABLE 5

Replicon Assay Data for UK-1 and its Analogs

| Compound | Virus | High Test Conc | Drug Units | $EC_{50}$ (µM) | $IC_{50}$ (µM) | $SI_{50}$ (µM) |
|---|---|---|---|---|---|---|
| 1 | HCV | 20 | µM | 0.21 | 11.6 | 55.3 |
| 8 | HCV | 20 | µM | 0.32 | 5.2 | 16.2 |

TABLE 5-continued

Replicon Assay Data for UK-1 and its Analogs

| Compound | Virus | High Test Conc | Drug Units | $EC_{50}$ (µM) | $IC_{50}$ (µM) | $SI_{50}$ (µM) |
|---|---|---|---|---|---|---|
| 9 | HCV | 20 | µM | 0.21 | 3.51 | 16.7 |
| rIFNa-2b | HCV | 2 | µM | 0.07 | >2 | >28.6 |
| 10 | HCV | 20 | µM | 1.41 | 6.32 | 4.5 |
| rIFNa-2b | HCV | 2 | µM | 0.04 | >2 | >50 |

Once the compounds proved active in the luciferase based replicon assay, they were analyzed in the RNA based confirmatory assay. The data shows slightly less inhibitory activity than in the presence of the DNA substrate, however the inhibitory activity is still comparable and the cytotoxicity is far less than that of the control rIFNa-2b (Table 3).

TABLE 6

RNA Based Confirmatory Assay Data for UK-1 and its Analogs

| Compound | Virus | High Test Conc | Drug Units | $EC_{50}$ (µM) | $IC_{50}$ (µM) | $SI_{50}$ (µM) |
|---|---|---|---|---|---|---|
| 1 | HCV | 20 | µM | 0.72 | >20 | >27.78 |
| 8 | HCV | 20 | µM | 0.58 | 5.18 | >8.93 |
| 9 | HCV | 20 | µM | | | |
| rIFNa-2b | HCV | 2 | µM | 0.24 | >2 | >8.34 |

Compounds 1, 8, 9, and 10 did not show any activity in the NTPase/helicase assay but were somehow still active against HCV in the replicon assay.

DEFINITIONS

As utilized herein, the following terms shall have the following meanings:

"Alkyl", alone or in combination, means a straight-chain or branched-chain alkyl radical containing preferably 1-15 carbon atoms ($C_1$-$C_{15}$), more preferably 1-8 carbon atoms ($C_1$-$C_8$), even more preferably 1-6 carbon atoms ($C_1$-$C_6$), yet more preferably 1-4 carbon atoms ($C_1$-$C_4$), still more preferably 1-3 carbon atoms ($C_1$-$C_3$), and most preferably 1-2 carbon atoms ($C_1$-$C_2$). Examples of such radicals include methyl, ethyl, n-propyl, isopropyl, n-butyl, isobutyl, sec-butyl, tert-butyl, pentyl, iso-amyl, hexyl, octyl and the like.

"Hydroxyalkyl", alone or in combination, means an alkyl radical as defined above wherein at least one hydrogen radical is replaced with a hydroxyl radical, preferably 1-3 hydrogen radicals are replaced by hydroxyl radicals, more preferably 1-2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1-2 double bonds and more preferably one double bond, and containing preferably 2-15 carbon atoms ($C_2$-$C_{15}$), more preferably 2-8 carbon atoms ($C_2$-$C_8$), even more preferably 2-6 carbon atoms ($C_2$-$C_6$), yet more preferably 2-4 carbon atoms ($C_2$-$C_4$), and still more preferably 2-3 carbon atoms ($C_2$-$C_3$). Examples of such alkenyl radicals include ethenyl, propenyl, 2-methylpropenyl, 1,4-butadienyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Aryl", alone or in combination, means a phenyl or naphthyl radical which is optionally substituted with one or more substituents selected from alkyl, alkoxy, halogen, hydroxy, amino, azido, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-CF$_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like.

"Aryloxy", alone or in combination, means a radical of the type "R—O—" wherein "R" is an aryl radical as defined above.

"Cycloalkyl", alone or in combination, means a saturated or partially saturated, preferably one double bond, monocyclic or bicyclic alkyl radical, preferably monocyclic, containing preferably 3-10 carbon atoms (C$_3$-C$_{10}$), more preferably 3-8 carbon atoms (C$_3$-C$_8$), even more preferably 3-6 carbon atoms (C$_3$-C$_6$), which is optionally be benzo fused and which is optionally substituted as defined herein with respect to the definition of aryl. Examples of such cycloalkyl radicals include cyclopropyl, cyclobutyl, cyclopentyl, cyclohexyl, dihydroxycyclohexyl, cycloheptyl, octahydronaphthyl, tetrahydronaphthyl, dimethoxytetrahydronaphthyl, 2,3-dihydro-1H-indenyl and the like.

"Heteroaryl", alone or in combination, means a monocyclic or bicyclic, preferably monocyclic, aromatic heterocycle radical, having at least one, preferably 1 to 4, more preferably 1 to 3, even more preferably 1-2, nitrogen, oxygen or sulfur atom ring member and having preferably 5-6 ring members in each ring, which is optionally benzo fused or saturated carbocyclic fused, preferably 3-4 carbon atoms (C$_3$-C$_4$) and which is optionally substituted as defined above with respect to the definitions of aryl and heterocyclyl. More preferably, "heteroaryl", alone or in combination, is a radical of a monocyclic or bicyclic aromatic heterocyclic ring system having 5-6 ring members per ring, wherein 1-3 ring members are oxygen, sulfur or nitrogen heteroatoms, which is optionally benzo-fused or saturated C$_3$-C$_4$-carbocyclic-fused. Examples of such heteroaryl groups include imidazolyl, 1-benzyloxycarbonylimidazol-4-yl, pyrrolyl, pyrazolyl, pyridyl, 2-(1-piperidinyl)pyridyl, 2-(4-benzyl piperazin-1-yl)-1-pyridinyl, pyrazinyl, triazolyl, furyl, thienyl, oxazolyl, thiazolyl, indolyl, quinolinyl, 1-oxido-2-quinolinyl, isoquinolinyl, 5,6,7,8-tetrahydroquinolyl, 5,6,7,8-tetrahydroisoquinolinyl, quinoxalinyl, benzothiazolyl, .beta.-carbolinyl, benzofuryl, benzimidazolyl, benzoxazolyl and the like.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl) benzene, 1,2-bis(dimethylsilyl)ethane and diphenylmethylsilyl. Sily lation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

Procedures for preparing the compounds of this invention are set forth below. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Preparation of Compounds of the Invention

Experimental Section

Materials and Methods

Melting points obtained with a Thomas-Hoover capillary melting point apparatus are uncorrected. $^1$H NMR and $^{13}$C NMR spectra recorded using a JEOL ECX 400 MHz NMR spectrometer. Chemical shifts reported in ppm. Ground-state absorption spectra recorded using a Beckman DU 640 UV/Vis spectrometer. Steady-state emission spectra obtained with an Edinburgh FLS920 fluorescence spectrometer equipped with a liquid-nitrogen-cooled PMT (Hamamatsu RS509). All spectral measurements performed at 25° C. Mass spectrometry analysis was performed on a Bruker Daltonics (Billerica, Mass., USA) Apex III Fourier transform ion cyclotron resonance (FT-ICR) mass spectometer equipped with a 7 Tesla actively shielded superconducting magnet and an Apollo electrospray source that has been modified in-house to enable low-flow operations and to include a heated metal capillary. Elemental analyses were performed by Atlantic Microlabs (Norcross, Ga.). Thin layer chromatography on EM Science silica gel 60 $F_{254}$ (0.20 mm) analytical glass plates. Fisher brand silica gel grade 60 Å (230-400 mesh) was used for flash chromatography, using a method by Still et al. All solvents and reagents were purchased from Fisher/Acros or Sigma Aldrich and used without purification unless otherwise noted.

Example 1

General Method for Carboxylating Naphthols

The commercial available dihydroxynaphthalenes and hydroxynaphthalene were added to a bomb reactor with magnesium methyl carbonate 2M in DMF. $N_2$ gas was blown into the reactor for 10 min. The reactor was sealed, placed in an oil bath and heated to 140° C. for 5-6 hours. The reactor was allowed to cool in an ice bath. The purple liquid and solid reaction mixture was then poured over ice. While stirring, 1M HCl was pipetted into the mixture until reaching pH ~1 resulting in an olive-green liquid with a precipitate. The mixture was filtered using a Büchner funnel and the solid cake was allowed to dry. After drying, the compound was dissolved in EtOAc (300 mL). The organic layers were combined and washed with $H_2O$ (3×100 mL) and saturated NaCl (1×200 mL). Product was dried over $Na_2SO_4$ and concentrated in vacuo.

Example 2

1,5-Dihydroxy-naphthalene-2-carboxylic Acid 1,5-dihydroxy-naphthalene (5.04 g, 31.4 mmol) and magnesium methyl carbonate (2 M in DMF, 34.0 mL), 273 g of ice, 2M HCl (85.0 mL)

Yield: 0.66 g of grey solid (10%). $^1$H NMR (400 MHz CDCl$_3$ w/3 drops DMSO) δ 2.49 (br s, 2H), δ 7.03 (dd, J=7.8 Hz, 1H), δ 7.31 (t, J=7.8 Hz, 1H), δ 7.67 (d, J=8.7 Hz, 1H), δ 7.75 (d, J=8.7 Hz, 1H), δ 7.86 (d, J=8.3 Hz, 1H), δ 9.30 (s, 1H), δ 12.45 (s, 1H).

Example 3

1,7-Dihydroxy-naphthalene-2-carboxylic Acid 1,7-Dihydroxy-naphthalene (2.58 g, 16.1 mmol) magnesium methyl carbonate, 1M HCl (38.0 mL). Yield: 1.38 g of grey solid (42%). $^1$H NMR (400 MHz, DMSO) δ 7.20 (dd, J=8.7 Hz, 2.8 Hz, 1H), δ 7.26 (d, J=8.7 Hz, 1H), δ 7.50 (d, J=6.4 Hz, 1H), δ 7.51 (d, J=6.4 Hz, 1H), δ 7.74 (d, J=8.7 Hz, 1H).

Example 4

General Method for Benzyl Protection

A stir bar and $K_2CO_3$ were placed in a 3-neck rbf, flame-dried and placed under $N_2$ gas. Dry DMF, the appropriate mono- or dihydroxy-naphthalene-2-carboxylic acid was added to the flask. Once the acid dissolved, benzyl chloride was added carefully to the reaction flask and the reaction stirred at 140° C. for 2-4 hours. Upon cooling, the reaction mixture was diluted with $H_2O$ (100 mL), turning cloudy. The mixture was extracted with EtOAc (3×200 mL), washed with $H_2O$ (5×200 mL) and saturated NaCl (1×200 mL). The product was dried over $Na_2SO_4$, filtered and concentrated by high vacuum. Purification by flash chromatography (50% Hexane/50% $CH_2Cl_2$). Solvent was removed under pressure and concentrated in vacuo.

Example 5

1,5-Bis-benzyloxy-naphthalene-2-carboxylic Acid Benzyl Ester $K_2CO_3$ (2.45 g, 17.7 mmol), Dry DMF (5.4 mL), 1,5-Dihydroxy-naphthalene-2-carboxylic acid (0.539 g, 2.64 mmol), benzyl chloride (1.5 mL) Yield: 0.68 g of product (54%, 2 steps) $R_f$=0.38 (SiO$_2$, 15% Hexanes/CH$_2$Cl$_2$). $^1$H NMR (400 MHz, CDCl$_3$) δ 5.12 (s, 2H), δ 5.25 (s, 2H), δ 5.40 (s, 2H), δ 6.98 (d, J=7.3 Hz, 1H), δ 7.30-7.53 (m, 16H), δ 7.83 (d, J=8.7 Hz, 1H), δ 7.89 (d, J=8.7 Hz, 1H), δ 8.14 (d, J=8.7 Hz, 1H).

Example 6

1,7-Bis-benzyloxy-naphthalene-2-carboxylic Acid Benzyl Ester $K_2CO_3$ (2.88 g, 20.0 mmol), dry DMF (6.4 mL), 1,7-Dihydroxy-naphthalene-2-carboxylic acid (0.635 g, 3.11 mmol), and benzyl chloride (1.72 mL). Yield: 0.805 g of golden brown viscous product (55%, 2 steps).

$R_f$=0.39 ($SiO_2$, 40% Hexanes/$CH_2Cl_2$), $^1$H NMR (400 MHz, $CDCl_3$) δ 4.99 (s, 2H), δ 5.06 (s, 2H), δ 5.40 (s, 2H), δ 7.28-7.52 (m, 16H), δ 7.56 (d, J=8.7 Hz, 2H), δ 7.75 (d, J=8.7 Hz, 1H), δ 7.78 (d, J=8.6 Hz, 1H); $^{13}$C NMR (400 MHz, $CDCl_3$) δ 67.04, 69.94, 103.21, 120.24, 121.78, 123.61, 124.64, 127.57, 128.12, 128.21, 128.27, 128.35, 128.52, 128.66, 128.70, 129.50, 130.01, 132.50, 136.07, 136.64, 137.55.

Example 7

General Method for the Selective Deprotection of 2-carboxylic Acid Benzyl Esters To a rbf containing MeOH (7.8 mL) and freshly prepared 40% aqueous NaOH (1.5 mL), the tribenzyl derivatives were added. A condenser was added and the reaction refluxed for 40-47 hours. The cooled, translucent brown reaction mixture was diluted with water, while stirring, citric acid was added, to approximately pH 4. The reaction mixture turned light brown in color and a precipitate formed. The mixture was extracted with EtOAc (3×100 mL), washed with $H_2O$ (2×100 mL) and saturated NaCl (1×100 mL), dried over $MgSO_4$, and filtered. The solvent was removed under pressure and concentrated in vacuo.

Example 8

1,5-Bis-benzyloxy-naphthalene-2-carboxylic Acid (4a)

1,5-Bis-benzyloxy-naphthalene-2-carboxylic acid benzyl ester (0.556 g, 1.17 mmol), MeOH (6.4 mL) and NaOH (1.25 mL), $H_2O$ (65.0 mL) and citric acid (0.28 g, 1.5 mmol) Yield: 0.507 g creamy white solid (92% yield). $^1$H NMR (400 MHz $CDCl_3$) δ 5.23 (s, 2H), δ 5.28 (s, 2H), δ 7.06 (d, J=7.3 Hz, 1H), δ 7.38-7.55 (m, 11H), δ 7.83 (d, J=8.7 Hz, 1H), δ 8.08 (d, J=8.7 Hz, 1H), δ 8.26 (d, J=8.7 Hz, 1H).

Example 9

1,7-Bis-benzyloxy naphthalene-2-carboxylic Acid (4b)

1,7-Bis-benzyloxy-naphthalene-2-carboxylic acid benzyl ester (0.749 g, 1.58 mmol). MeOH (8.5 mL) and NaOH (1.7 mL), $H_2O$ (60.0 mL), citric acid (3.91 g, 20.4 mmol) Yield: 0.549 g of an off-white flaky solid (90% yield). $^1$H NMR (400 MHz, $CDCl_3$) δ 5.12 (s, 2H), δ 5.14 (s, 2H), δ 7.30-7.51 (m, 12H), δ 7.68 (d, J=8.7 Hz, 1H), δ 7.84 (d, J=8.7 Hz, 1H), δ 7.96 (d, J=8.2 Hz, 1H).

Example 10

General Method for Coupling Using Carbonyldiimidazole (CDI)

CDI 97% was dissolved in dry THF in a flame-dried 3-neck rbf. Stirring at room temperature under $N_2$ gas, the mono- or dibenzyloxy naphthoic acids were added slowly to the mixture. The reaction mixture stirred for approximately 10 minutes after $CO_2$ ceased (15 minutes total). Then 2-amino-3-hydroxy-benzoic acid methyl ester was added and allowed to stir for 10 minutes before the reaction was heated to reflux for 20-25 hours. The reaction mixture was diluted with $H_2O$ (50 mL), then extracted with $CH_2Cl_2$ (3×50 mL). The organic layers were combined and washed with $H_2O$ (1×50 mL) and saturated NaCl (1×50 mL), dried over $Na_2SO_4$ and filtered. Purification by flash chromatography (20% Hexanes/80% $CH_2Cl_2$). Solvent was removed under pressure and concentrated in vacuo.

Example 11

2[(1,5-Bis-benzyloxy-naphthalene-2-carboxyl)-amino)]-3-hydroxy-benzoic Acid Methyl Ester CDI (0.245 g, 1.51 mmol), dry THF (7.4 mL) compound 4 (0.484 g, 1.26 mmol), 2-amino-3-hydroxy-benzoic acid methyl ester (0.211 g, 1.26 mmol) Yield: 0.225 g of viscous, reddish-brown product (33% yield). $R_f$=0.40 ($SiO_2$, 20% Hexanes/80% $CH_2Cl_2$), $^1$H NMR (400 MHz, $CDCl_3$) δ 3.77 (s, 3H), δ 5.18 (s, 2H), δ 5.29 (s, 2H), δ 7.03 (d, J=7.8 Hz, 1H), δ 7.21 (t, J=7.8 Hz, 1H) δ 7.32 (dd, J=9.6 Hz, 1.4 Hz, 1H), δ 7.36-7.39 (m, 3H), δ 7.42-7.49 (m, 3H), δ 7.54 (d, J=7.3 Hz, 2H), δ 7.60 (dd, J=7.8 Hz, 1.4 Hz, 1H), δ 7.91 (d, J=8.7 Hz, 1H), δ 8.03 (d, J=8.7 Hz, 1H), δ 8.24 (d, J=8.7 Hz, 1H).

Example 12

2[((1,7-bis-benzyloxy-napthalene-2-carboxyl)-amino)]-3-hydroxy-benzoic Acid Methyl Ester CDI (g, mmol), dry THF (7.4 mL), compound 5 (0.488 g, 1.27 mmol), 2-amino-3-hydroxy-benzoic acid methyl ester (0.213 g, 1.27 mmol). Yield: 0.290 g of viscous, reddish-brown product (43% yield). $R_f$=0.31 ($SiO_2$, 20% Hexanes/80% $CH_2Cl_2$), $^1$H NMR (400 MHz, $CDCl_3$) δ 3.80 (s, 3H), δ 5.10 (s, 2H), δ 5.29 (s, 2H), δ 7.22 (t, J=7.8 Hz, 1H), δ 7.27-7.43 (m, 12H), δ 7.56 (d, J=2.2 Hz, 1H), δ 7.61 (dd, J=7.8 Hz, 1.8 Hz, 1H), δ 7.67 (d, J=8.7 Hz, 1H), δ 7.81 (d, J=8.7 Hz, 1H), δ 7.92 (d, J=8.7 Hz, 1H).

Example 13

General Method for Cyclodehydration

In a flame-dried round bottom flask (rbf), amide compound from coupling reactions were dissolved in anhydrous m-xylene, then pyridium p-toluenesulfonate (PPTS) was added. The mixture refluxed for 4-9 hours under nitrogen (Note: 9 hour reaction resulted in a mixture of cyclized benzyl protected and unprotected product). The reaction mixture was diluted with 75 mL of $CH_2Cl_2$ and place in a separatory funnel. $NaHCO_3$ (75 mL) was added then the product was extract with $CH_2Cl_2$ (3×50 mL). The combined organic layers were washed with $H_2O$ (2×50 mL) and saturated NaCl (1×50 mL), dried over $Na_2SO_4$ and filtered. The solvent was removed under reduced pressure and additional drying completed in vacuo. Purification by flash chromatography (100% $CH_2Cl_2$).

Example 14

2-(5-Benzyloxy-1-hydroxy-naphthalene-2-yl)-benzoxazole-4-carboxylic Acid Methyl Ester (2a)

2[(1,5-Bis-benzyloxy-naphthalene-2-carboxyl)-amino)]-3-hydroxy-benzoic acid methyl ester (0.223 g, 0.418 mmol), anhydrous m-xylene (3.4 mL), PPTS (0.212 g, 0.836 mmol) was added. The mixture refluxed for 5 hours under $N_2$ (g). After purification by flash chromatography, Yield: 0.110 g of yellow solid (52% yield, 2 steps): $R_f$=0.34 ($SiO_2$, 100% $CH_2Cl_2$), m.p. 183.5-185° C.; $^1$H NMR (400 MHz, $CDCl_3$) δ 4.10 (s, 3H), δ 5.27 (s, 2H), δ 7.06 (d, J=7.3 Hz, 1H), δ 7.35-7.55 (m, 7H), δ 7.83 (dd, J=8.7 Hz, 1 Hz, 1H), δ 7.96 (q, J=8.7 Hz, 2H), δ 8.09 (dd, J=7.3 Hz, 1 Hz, 1H), δ 8.11 (d, J=8.2 Hz, 1H) $^{13}$C NMR (100 MHz, $CDCl_3$) δ 52.44, 70.37, 103.74, 108.65, 113.69, 114.88, 116.18, 120.96, 121.41, 124.41, 126.09, 127.44, 128.06, 128.48, 128.65, 136.87, 139.62, 149.85, 154.32, 157.86, 165.26, 165.69; Anal. calcd for $C_{26}H_{19}NO_5$: C, 73.40; H, 4.50; N, 3.29. Found: C, 73.43; H, 4.51; N, 3.17.

Example 15

2-(7-benzyloxy-1-hydroxy-napthalen-2-yl)-benzoxazole-4 Carboxylic Acid Methyl Ester (2b)

2[((1,7-bis-benzyloxy-napthalene-2-carboxyl)-amino)]-3-hydroxy-benzoic acid methyl ester (0.290 g, 0.544 mmol), anhydrous m-xylene (4.4 mL), PPTS (0.275 g, 1.09 mmol) The reaction was refluxed at 140° C. for 4 hours. As the reaction mixture cooled it became cloudy and a yellowish-brown precipitant formed. The reaction mixture was diluted with 50 mL of $CH_2Cl_2$ and place in a separatory funnel. $NaHCO_3$ (50 mL) was added to the mixture then the product was extracted with $CH_2Cl_2$ (3×50 mL). The organic layers were combined and washed with $H_2O$ (4×50 mL) and saturated NaCl (1×50 mL). Dried over $NaSO_4$ and concentrated in vacuo using a coldfinger. Purification was completed by flash chromatography using a gradient elution starting with 40% Hexanes/$CH_2Cl_2$ and ending with 10% Hexanes/$CH_2Cl_2$ dropping the percentage of hexanes in increments of 10 until four different fractions were collected. $^1$H NMR on two sets of fractions collected showed that 0.074 g of the monobenzylated compound (2b) m.p. −181.5-183° C.; $^1$H NMR (400 MHz, $CDCl_3$) δ 4.10 (s, 3H), δ 5.27 (s, 2H), δ 7.34-7.47 (m, 6H), δ 7.53 (d, J=7.3 Hz, 2H) δ 7.75 (d, J=9.2 Hz, 1H), δ 7.82 (dd, J=8.3 Hz, 1 Hz, 1H), δ 7.88 (d, J=8.3 Hz, 1H), δ 7.91 (d, J=2.2 Hz, 1H), δ 8.09 (dd, J=7.8 Hz, 1 Hz, 1H); $^{13}$C NMR (100 MHz, $CDCl_3$) δ 52.44, 70.37, 103.26, 103.53, 114.85, 119.20, 119.91, 120.95, 121.96, 124.39, 127.39, 127.80, 128.13, 128.65, 129.33, 131.86, 136.69, 139.66, 149.86, 157.14, 165.25, 165.68. Anal. calcd for $C_{26}H_{19}NO_5$: C, 73.40; H, 4.50; N, 3.29. Found: C, 72.81; H, 4.43; N, 3.22 and 0.104 g of the dibenzylated compound (5b) were achieved (34.4% and 48% yield, respectively).

Example 16

General Method for Catalytic Hydrogenation

In a parr shaker bottle, (27) was dissolve using EtOAc, 10% Palladium on carbon (Pd/C) was added to the solution. The reaction mixture was then placed on the parr shaker with 30 psi of $H_2$ gas for 3-6 hours. In general a total of 0.5-2 psi of $H_2$ gas was consumed. Pd/C was filtered over celite using a Büchner Funnel. The solvent was removed under pressure and concentrated in vacuo.

Example 17

2-(5-Benzyloxy-1-hydroxy-naphthalene-2-yl)-benzoxazole-4-carboxylic Acid Methyl Ester (2a)

2[(1,5-Bis-benzyloxy-naphthalene-2-carboxyl)-amino)]-3-hydroxy-benzoic acid methyl ester (0.030 g, 0.058 mmol), 10% Pd/C (0.010 g, 0.94 mmol), EtOAc (10 mL). Purification by prep plate. Yield: 0.012 g of yellow solid (90%).

Example 18

1-Benzyloxy-naphthalene-2-carboxylic Acid Benzyl Ester $K_2CO_3$ (9.26 g, 67 mmol), dry DMF (20 mL), commercially available 1-hydroxy-2-naphthoic acid (1.88 g, 10 mmol), and benzyl chloride (5.6 mL). Yield: 1.41 g of yellow-orange viscous product (38.5% yield). $R_f$=0.38 ($SiO_2$, 50% Hexanes/50% $CH_2Cl_2$). $^1$H NMR (400 MHz, $CDCl_3$) δ 5.13 (s, 2H), δ 5.39 (s, 2H), δ 7.32-7.41 (m, 7H), δ 7.43-7.52 (m, 5H) δ 7.57 (d, J=7.8 Hz, 1H), δ 7.63 (d, J=8.7 Hz, 1H), δ 7.84 (d, J=8.2 Hz, 1H), δ 7.92 (d, J=8.7 Hz, 1H), δ 8.24 (d, J=8.2 Hz, 1H).

Example 19

1-Benzyloxy-naphthalene-2-carboxylic Acid

Method slightly modified, THF (30 mL) instead of MeOH and 5M NaOH (32 mL) were added to the rbf containing compound 1-Benzyloxy-naphthalene-2-carboxylic acid benzyl ester (1.40 g, 3.80 mmol). A condenser was added and the mixture was refluxed for 9 hours. The mixture was diluted with $H_2O$ (100 mL) and citric acid (17.70 g, 92.12 mmol) was added to pH-4. Extracted with $CH_2Cl_2$ (3×100 mL), washed with $H_2O$ (2×150 mL) and saturated NaCl (1×150 mL). NMR showed final product with small percent of starting material. Purification was achieved by recrystallization in hexanes (2×20 mL). Solvent removed under pressure and concentrated in vacuo. Yield: 0.652 g of white crystals (62%). $^1$H NMR (400 MHz, $CDCl_3$) δ 5.24 (s, 2H), δ 7.43-7.54 (m, 3H), δ 7.61-7.68 (m, 2H), δ 7.75 (d, J=8.7 Hz, 1H), δ 7.93 (dd, J=7.3 Hz, 1 Hz, 1H), δ 8.10 (d, J=8.7 Hz, 1H), δ 8.25 (d, J=7.8 Hz, 1H).

Example 20

2[((1-benzyloxy-napthalene-2-carboxyl)-amino)]-3-hydroxy-benzoic Acid Methyl Ester CDI (0.195 g, 1.2 mmol), dry THF (5.8 mL), 1-benzyloxy-naphthalene-2-carboxylic acid (0.278 g, 1 mmol). 2-amino-3-hydroxy-benzoic acid methyl ester (0.167 g, 1 mmol) Yield: 0.240 g of viscous, reddish-brown product (56% yield). $R_f$=0.56 ($SiO_2$, 3% EtOAc/$CH_2Cl_2$), $^1$H NMR (400 MHz, $CDCl_3$) δ 3.78 (s, 3H), δ 5.19 (s, 2H), δ 7.22 (t, J=7.8 Hz, 1H), δ (m, 3H), δ 7.57-7.65 (m, 3H), δ 7.75 (d, J=8.7 Hz, 1H), δ 7.91 (d, J=7.8 Hz, 1H), δ 8.07 (d, J=8.7 Hz, 1H), δ 8.33 (d, J=7.8 Hz, 1H), δ 9.39 (s, 1H), δ 12.29 (s, 1H).

Example 21

2-(1-benzyloxy-naphthalen-2-yl)benzoxazole-4-carboxylic Acid Methyl Ester

2[((1-benzyloxy-napthalene-2-carboxyl)-amino)]-3-hydroxy-benzoic acid methyl ester (0.240 g, 0.561 mmol), anhydrous m-xylene (4.6 mL), PPTS (0.283 g, 1.12 mmol) The bright yellow reaction mixture refluxed for 4 hours. The reaction mixture was transferred to a separatory funnel and 50 mL of $NaHCO_3$ was added. The product was extracted with $CH_2Cl_2$ (3×50 mL). The combined organic layer were washed with $H_2O$ (4×50 mL) and saturated NaCl (1×50 mL), dried over Na$_2$SO$_4$, and filtered. The solvent was removed under pressure and concentrated in vacuo. Purification was completed by flash chromatography. Yield: 0.096 g of dark yellow viscous liquid (42%). R$_f$=0.42 (SiO$_2$, 3% EtOAc/CH$_2$Cl$_2$), $^1$H NMR (400 MHz, CDCl$_3$) δ 3.96 (s, 3H), δ 5.28 (s, 2H), δ 7.37-7.46 (m, 4H), δ 7.55-7.64 (m, 4H), δ 7.73 (dd, J=7.8 Hz, 1 Hz, 1H), δ 7.78 (d, J=8.7 Hz, 1H), δ 7.91 (d, J=7.8 Hz, 1H), δ 8.07 (dd, J=8.7 Hz, 1 Hz, 1H), δ 8.33 (d, J=8.3 Hz, 1H), δ 8.37 (d, J=8.7 Hz, 1H).

Example 22

2-(1-Hydroxy-naphthalen-2-yl)benzoxazole-4-carboxylic Acid Methyl Ester (6)

2-(1-benzyloxy-naphthalen-2-yl)benzoxazole-4-carboxylic acid methyl ester, EtOAc (15.4 mL). 10% Pd/C (0.041 g, 0.376 mmol), 0.5 psi of H$_2$(g) was consumed. Yield: 0.059 g of orange-yellow solid (75%). m.p. −185-186.5° C.; $^1$H NMR (400 MHz, CDCl$_3$) δ 4.10 (s, 3H), δ 7.42-7.46 (m, 2H), δ 7.57-7.62 (m, 2H), δ 7.82 (d, J=8.3 Hz, 2H), δ 8.00 (d, J=8.7 Hz, 1H), δ 8.08 (dd, J=7.8 Hz, 1 Hz, 1H), δ 8.52 (d, J=8.2 Hz, 1H); $^{13}$C NMR (100 MHz, CDCl$_3$) δ 52.45, 103.11, 114.83, 119.42, 120.95, 122.10, 123.93, 124.38, 126.05, 127.40, 127.68, 129.06; Anal. calcd for C$_{19}$H$_{13}$NO$_3$ C, 71.47; H, 4.10; N, 4.39. Found C, 71.40; H, 4.12; N, 4.29.

Synthesis of Negative Control by Modified Method

Example 23

2-Naphthalen-2-yl-benzoxazole-4-carboxylic Acid Methyl Ester (7)

In a flame dried rbf charged with nitrogen, a mixture of 2-naphthoic acid (0.516 g, 3 mmol), anhydrous m-xylene (14.83 mL) and thionyl chloride (11 mL) were refluxed for 2 hours. R$_f$=TLC (SiO$_2$, 5% EtOAc/CH$_2$Cl$_2$) showed reaction was complete. The solvent was removed in vacuo resulting in 0.604 g of creamy white crystals of 2-naphthoyl chloride (100% yield). Fresh anhydrous m-xylene (5 mL) was added to 2-naphthoyl chloride (0.416 g, 2 mmol) and allowed to stir for 5 minutes, then a mixture of 2-amino-3-hydroxy-benzoic acid methyl ester (0.334 g, 2 mmol), triethylamine (3 mL) were added. The mixture was allowed to stir at room temperature for 4 hours, then the reaction mixture was heated to reflux and allowed to stir at refluxed temperature for 12 hours. The cooled mixture diluted with 100 mL of EtOAc and transferred to a separatory funnel, washed with of 0.1 M HCl (1×50 mL), H$_2$O (1×50 mL) saturated NaHCO$_3$ (1×50 mL), H$_2$O (1×50 mL), and saturated NaCl (1×50 mL), respectively. The product was dried over Na$_2$SO$_4$; solvent was removed under pressure and concentrated in vacuo. The resulting 0.578 g of reddish-brown product was placed in a flame-dried rbf under N$_2$ (g), then anhydrous m-xylene (14.4 mL), and PPTS (0.904 g, 3.6 mmol) were added. The reaction mixture refluxed for 4 hours. The cooled mixture was diluted with 100 mL EtOAc and transferred to a separatory funnel, washed with saturated NaHCO$_3$ (1×50 mL), H$_2$O (4×50 mL), and saturated NaCl (1×50 mL), dried over Na$_2$SO$_4$; solvent was removed under pressure and concentrated in vacuo using a coldfinger. The mixture was purified using flash chromatography Yield: 0.173 g tan solid (28% yield, 4 steps). R$_f$=0.40 (SiO$_2$, 3% EtOAc/CH$_2$Cl$_2$). $^1$H NMR (400 MHz, CDCl$_3$) δ 4.09 (s, 3H), δ 7.44 (t, J=7.8, 1H), δ 7.58-7.60 (m, 2H), δ 7.82 (dd, J=9.2 Hz, 1 Hz, 2H), δ 7.90 (d, J=7.3 Hz, 1H), δ 7.98-8.06 (m, 3H), δ 8.41 (dd, J=8.7 Hz, 1.8 Hz, 1H), δ 8.89 (s, 1H).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

c. Assays

NTPase/Helicase Assay:

NTPase/Helicase activity determined by a previously described method. Helicase activity was determined as a function of increasing concentrations of the compounds in the presence of ATP adjusted to 105 µM, 235 µM, for HCV, JEV, and DENV NTPase/Helicase, respectively and 4.7 M of DNA substrate (concentration of nucleotide base). The substrate and released strand were separated in TBE polyacrylamide gel and visualized by exposition of dried gel onto X-ray film for 20 h. The part of the gels corresponding to the released strand were excised, and the $^{32}$P radioactivity was quantified.

Replicon Assay:

In the replicon assays a Huh7 ET (luc-ubi-neo/ET) cell line is used. This particular construct contain the 5'NTR (IRES) of HCV, producing a firefly luciferase (luc), ubiquitin (ubiq) and neomycin phosphotranferase (neo) fusion protein. This modification makes the cell line more robust and provides the additional stability needed for antiviral screening. The effects of the drug were examined in triplicate at a single high-test concentration of 20 µM on HCV RNA-derived LUC activity and cytotoxicity.

This invention also relates to a pharmaceutical composition and medicaments comprising a compound of this invention and a pharmaceutically acceptable carrier, and if desired other active ingredients. The compounds of this invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art.

The present invention further features pharmaceutical compositions comprising a compound of the invention (or a salt, solvate or prodrug thereof) and another therapeutic agent. In a non-limiting example, a pharmaceutical composition of the present invention includes 1, 2, 3 or more compounds of the invention (or salts, solvates or prodrugs thereof), and 1, 2, 3 or more other therapeutic agents. By way of illustration not limitation, these other therapeutic agents can be selected from antiviral agents (e.g., anti-HIV agents or other anti-HCV agents), immunomodulators, anti-cancer or chemotherapeutic agents, or anti-inflammation agents. Specific examples of these other therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals); compound VX-950, Vertex Pharmaceuticals Inc.); compound SCH503034, Schering-Plough Co.); and compound GS9137, Gilead Sciences, Inc., Foster City, Calif.). Any other desirable therapeutic agent(s) can also be included in a pharmaceutical composition of the present invention.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents independently selected from HCV RNA dependent RNA polymerase inhibitors (e.g., nucleoside or non-nucleoside type polymerase inhibitors), HCV protease inhibitors, or HCV helicase inhibitors.

In a further embodiment, a pharmaceutical composition of the present invention comprises one or more compounds of the present invention (or salts, solvates or prodrugs thereof), and two or more other anti-HCV inhibitors selected from the same inhibitor class (e.g., all of them are selected from HCV RNA dependent RNA polymerase inhibitors, or from HCV protease inhibitors), or selected from different inhibitor classes (e.g., one or more are selected from HCV RNA dependent RNA polymerase inhibitor and the other or others are selected from HCV protease inhibitors).

In still another embodiment, a pharmaceutical composition of the present invention comprises at least one compound of the present invention (or a salt, solvate or prodrug thereof), and at least one HCV RNA dependent RNA polymerase inhibitor.

In another embodiment, a pharmaceutical composition of the present invention comprises at least one compound of the present invention (or a salt, solvate or prodrug thereof), and at least one HCV protease inhibitor.

In yet another embodiment, a pharmaceutical composition of the present invention comprises at least one compound of the present invention (or a salt, solvate or prodrug thereof), at least one HCV RNA dependent RNA polymerase inhibitor, and at least one HCV protease inhibitor.

In still yet another embodiment, a pharmaceutical composition of the present invention comprises at least one compound of the present invention (or a salt, solvate or prodrug thereof), and two or more anti-HCV agents each of which is independently selected from HCV RNA dependent RNA polymerase inhibitors or HCV protease inhibitors.

In still another embodiment, a pharmaceutical composition of the present invention comprises at least one compound of the present invention (or a salt, solvate or prodrug thereof), and three or more other anti-HCV agents each of which is independently selected from HCV RNA dependent RNA polymerase inhibitors or HCV protease inhibitors.

Non-limiting examples of HCV RNA dependent RNA polymerase inhibitors include those described in WO0190121(A2), U.S. Pat. No. 6,348,587B1, WO0160315, WO0132153, EP1162196A1 and WO0204425. Non-limiting examples of HCV protease inhibitors include BILN-2061, VX-950, and SCH503034.

In another embodiment, a pharmaceutical composition of the present invention comprises at least one compound of the present invention (or a salt, solvate or prodrug thereof), and one or more other antiviral agents, such as anti-HBV or anti-HIV agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, and other HIV protease, reverse transcriptase, integrase or fusion inhibitors. Other desirable antiviral agents can also be included in a pharmaceutical composition of the present invention, as appreciated by those skilled in the art.

The inventive subject matter contemplates combination therapy. The phrase "combination therapy" (or "co-therapy"), is intended to embrace administration of each agent in a sequential manner in a regimen that will provide beneficial effects of the drug combination, and is intended as well to embrace co-administration of these agents in a substantially simultaneous manner, such as by oral ingestion or a single capsule having a fixed ratio of these active agents or ingestion of multiple, separate capsules for each agent. "Combination therapy" will also include simultaneous or sequential administration by oral, intravenous, intramuscular or other parenteral routes into the body, including direct absorption through mucous membrane tissues, as found in the sinus passages. Sequential administration also includes drug combinations where the individual agents may be administered at different times and/or by different routes but which act in combination to provide a beneficial effect, for example, by co-action of pharmacokinetic or pharmacodynamic effects of each agent.

The dosage regimen for treating a disease state with the compounds of this invention and/or compositions of this invention is based on a variety of factors, including the type of disease, the age, weight, sex and medical condition of the patient, the severity of the condition, the route of administration, pharmacological considerations such as the activity, efficacy, pharmacokinetic and toxicology profiles of the particular compound employed, whether a drug delivery system is utilized and whether the compound is administered as part of a drug combination. Thus the dosage regimen may vary widely. Dosage levels of the order from about 0.01 mg to 80 mg per kilogram of body weight per day, preferably from about 0.5 mg to 30 mg/kg, more preferably from about 1 mg to 15 mg/kg are useful for all methods of use disclosed herein. The pharmaceutically active compounds of this invention can be processed in accordance with conventional methods of pharmacy to produce medicinal agents for administration to patients, mammals including humans.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 250 mg, preferably from about 25 to 150 mg. A suitable daily dose for a human or other mammal may vary widely depending on the condition of the patient and other factors.

The compounds of this invention may also be administered by injection as a composition with suitable carriers including saline, dextrose, or water. The daily parenteral dosage regimen will be from about 0.1 to about 80 mg/kg of total body weight, preferably from about 0.5 to about 30 mg/kg, and more preferably from about 1 mg to 15 mg/kg.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

A suitable topical dose of compounds of this invention is 0.1 mg to 150 mg administered one to four, preferably two or three times daily. For topical administration, the active ingredient may comprise from 0.001% to 10% w/w, e.g. from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin such as liniments, lotions, ointments, creams, or pastes and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, benzyl alcohol, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form including granules, powders or suppositories or in a liquid form such as solutions, suspensions, or emulsions. The pharmaceutical compositions may be subjected to conventional pharmaceutical operations such as sterilization and/or may contain conventional adjuvants, such as preservatives, stabilizers, wetting agents, emulsifiers, buffers, etc.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of this invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of this invention can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more other agents. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

REFERENCES (1) De Francesco, R., and Migliaccio, G. *Nature* 2005, 436, 953-960.
(2) WHO; J. Viral Hepatitis, 1999, 6: 35-47.
(3) NIH; NIH Publication No. 09-4229: 2009; Vol. 2009.
(4) Frick, D. N. *Curr. Issues Mol. Biol.* 2007, 9, 1-20.
(5) Sakamoto, N., and Watanabe, M. *J Gastroenterol* 2009, 44, 643-649.
(6) Wardell, A. D., Errington, W., Ciaramella, G., Merson, J., and McGarvey M. J. *J. General Virology* 1999, 80, 701-709.
(7) Gordon, C. P., and Keller, P. A. *Journal of Medicinal Chemistry* 2005, 48, 1-20.
(8) Zhang, N., Chen, H-M., Koch, V., Schmitz, H., Liao, C-L., Bretner, M., Bhadti, V. S., Fattom, A. I., Naso, R. B., Hosmane, R. S., Borowski, P. *J. Med. Chem.* 2003, 46, 4149-4164.
(9) Zhang, P., Zhang, N., Buckwold, V. E., and Hosmane, R. S. *Bioorg. Med. Chem.* 2007, 15, 4933-4945.
(10) Reynolds, M., DeLuca, M., and Kerwin, S. M. *Bioorg. Chem.* 1999, 27, 326-337.
(11) Ueki, M., Ueno, K., Miyadoh, S., Abe, Shibata, K., Tanguchi, M., and Oi, S. *J. Antibiotics* 1993, 46, 1089-1094.
(12) Sehested, M. a. J., P. B. *Biochem. Pharm.* 1996, 51, 879-886.
(13) Yedavalli, V. S. R. K., Zhang, N., Cai, H., Zhang, P., Starost, M. F., Hosmane, R. S., and Jeang, K-T. *Journal of Medicinal Chemistry* 2008, 51, 5043-5051.
(14) Marchand, C., Johnson, A., Karki, R., Pais, G. C., Zhang, X., Cowansage, K., Patel, T., Nicklaus, M., Burke Jr., T., and Pommier, Y. *Mol. Pharma.* 2003, 64, 600-609.
(15) Maurin, C., Bailly, F., and Cotelle, P. *Curr. Med. Chem.* 2003, 10, 1795-1810.
(16) Grobler, J. A., Stillmock, K., Hu, B., Witmer, M., Felock, P., Espeseth, A. S., Wolfe, A., Egbertson, M., Bourgeois, M., Melamed, J., Wai, J. S., Young, S., Vacca, J., and Hazuda, D. J. *Proc. Natl. Acad. Sci. USA* 2002, 99, 6661-6666.
(17) Kumar, D., Jacob, M. R., Reynolds, M. B, and Kerwin, S. M. *Bioorg. Med. Chem. Lett.* 2002, 10, 3997-4004.
(18) Wang, B., Maghami, N., Goodlin, V., and Smith, P. J. *Bioorg. Med. Chem. Lett.* 2004, 14, 3221-3226.
(19) Cate, L. A. *Synthesis* 1983, 385-386.
(20) Henary, M. M., and Fahrni, C. J. *J. Phys. Chem. A.* 2002, 106, 5210-5220.
(21) Borowski, P., Kuehl, R., Mueller, O., Hwang, L-H., Schulze zur Wiesch, J. *Eur. J. Biochem.* 1999, 266, 715-723.
(22) Borowski, P., Mueller, O., Niebhr, A., Kalitzky, M., Hwang, L-H. *Acta Biochim. Polon.* 2000, 47, 173-180.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

We claim:

1. A compound, which comprises:

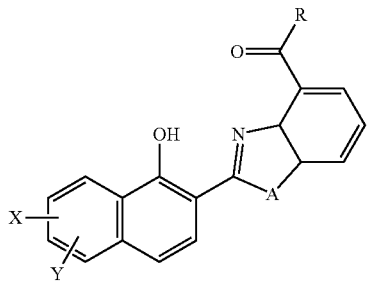

wherein
A is N, S, or O;
R is independently a hydrogen, amino, alkylamino, dialkylamino, hydroxy, or alkoxy radical; and,
X and Y are independently a hydrogen, amino, alkylamino, dialkylamino, alkylacylamino, hydroxy, alkoxy, alkyl, alkenyl, or arylacylamino radical optionally substituted by 1-3 radicals of alkyl, alkenyl, amino, alkylamino, hydroxy, alkoxy, aryl or heteroaryl.

2. The compound of claim 1 or a pharmaceutically acceptable salt thereof,
wherein
R is independently a hydrogen hydroxy, aminoalkyl, or alkoxy radical; and,
X and Y are independently a hydrogen, alkyl, aryl, alkoxy, aryloxy, alkylamino, arylamino, alkylacylamino or arylacylamino radical.

3. The compound of claim 1 or a pharmaceutically acceptable salt thereof,
wherein
A is O;
R is independently a hydroxy, aminoalkyl, or alkoxy radical;
X is a benzyloxy radical; and
Y is a hydrogen radical.

4. A pharmaceutical composition comprising a compound of claim 1 and a pharmaceutically acceptable carrier.

5. A method of treatment of Hepatitis C Virus infection in a mammal, comprising administering an effective amount of the compound of claim 1.

6. A method of treatment of Hepatitis C Virus infection in a mammal, comprising administering an effective amount of the pharmaceutical composition of claim 4.

7. A method of treatment of Hepatitis C Virus infection in a mammal, comprising administering an effective amount of the compound selected from the group consisting of:

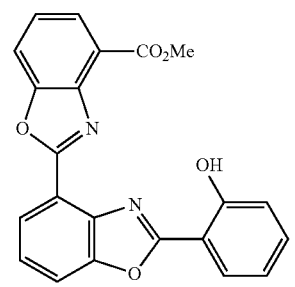

1

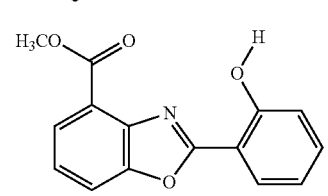

8

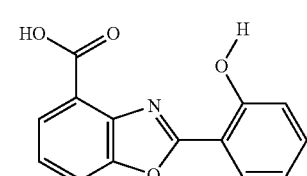

9

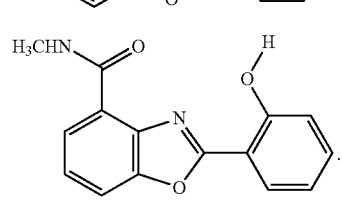

10

* * * * *